(12) United States Patent
Belanoff

(10) Patent No.: US 8,741,880 B2
(45) Date of Patent: Jun. 3, 2014

(54) ANTIGLUCOCORTICOID THERAPY FOR THE PREVENTION OF NEUROLOGICAL DAMAGE IN PREMATURE INFANTS

(75) Inventor: Joseph K. Belanoff, Woodside, CA (US)

(73) Assignee: Corcept Therapeutics, Inc., Menlo Park, CA (US)

(*) Notice: Subject to any disclaimer, the term of this patent is extended or adjusted under 35 U.S.C. 154(b) by 0 days.

(21) Appl. No.: 13/034,478

(22) Filed: Feb. 24, 2011

(65) Prior Publication Data

US 2011/0144072 A1    Jun. 16, 2011

Related U.S. Application Data

(63) Continuation of application No. 12/238,751, filed on Sep. 26, 2008, now abandoned, which is a continuation of application No. 10/896,149, filed on Jul. 20, 2004, now abandoned.

(60) Provisional application No. 60/489,601, filed on Jul. 23, 2003.

(51) Int. Cl.
    *A61K 31/56*      (2006.01)

(52) U.S. Cl.
    USPC .......................................... 514/170; 514/182

(58) Field of Classification Search
    USPC ................................................. 514/170, 182
    See application file for complete search history.

(56) References Cited

U.S. PATENT DOCUMENTS

| 2002/0151588 A1 | 10/2002 | Thomson et al. |
| 2002/0169152 A1 | 11/2002 | Belanoff |
| 2003/0064973 A1 | 4/2003 | Patchev et al. |
| 2004/0266863 A1 | 12/2004 | Sennef et al. |

OTHER PUBLICATIONS

Barrington, K., "Hazards of systemic steroids for ventilator-dependent preterm infants: What would a parent want?" *Canadian Medical Association Journal*, 2001, pp. 33-34, vol. 165, No. 1.
Barrington, Keith J., "The adverse neuro-developmental effects of postnatal steroids in the preterm infant: a systematic review of RCTs," Feb. 27, 2001, BMC Pediatrics, 2001, 1:1.
Committee on Fetus and Newborn, "Postnatal Corticosteriods to Treat or Prevent Chronic Lung Disease in Preterm Infants," *Pediatrics*, 2002, pp. 3308-3338, vol. 109.
Grier, David G. and Henry L. Halliday, "Corticosteroids in the Prevention and Management of Bronchopulmonary Dysplasia," Seminars in Neonatology, vol. 8, pp. 83-91, (2003).
Lazar, Jr. G, "The antiglucocorticoid RU 38486 Reverses the Wasting Syndrome in Newborn Rats," May 4, 1992, Naturwissenschaften, 79, pp. 472-473.
Murphy, B., et al., "Impaired Cerebral Cortical Gray Matter Growth After Treatment With Dexamethasone for Neonatal Chronic Lung Disease," *Pediatrics*, 2001, pp. 217-221, vol. 107.
Yeh, T. et al., "Early Postnatal Dexamethasone Therapy for the Prevention of Chronic Lung Disease in Preterm Infants With Respiratory Distress Syndrome: A Multicenter Clinical Trial," *Pediatrics*, 1997, pp. E3, vol. 100.
Yeh, T., et al., "Early Dexamethasone Therapy in Preterm Infants: A Follow-up Study," *Pediatrics*, 1998, pp. E7, vol. 101.

*Primary Examiner* — San-Ming Hui
(74) *Attorney, Agent, or Firm* — Kilpatrick Townsend & Stockton LLP

(57) ABSTRACT

This invention pertains to the discovery that agents which inhibit the binding of cortisol to its receptors can be used in methods for preventing neurological damage associated with glucocorticoid therapy in ventilator-dependent low birth weight preterm infants. Mifepristone, a potent glucocorticoid receptor antagonist, can be used in these methods.

15 Claims, No Drawings

ANTIGLUCOCORTICOID THERAPY FOR THE PREVENTION OF NEUROLOGICAL DAMAGE IN PREMATURE INFANTS

CROSS-REFERENCES TO RELATED APPLICATIONS

This application claims the benefit under 35 U.S.C. §119(e) of U.S. Provisional Application No. 60/489,601, filed Jul. 23, 2003.

FIELD OF THE INVENTION

This invention is directed to a method for preventing neurological damage in a ventilator-dependant low birth weight preterm infant in need of postnatal glucocorticoid therapy.

BACKGROUND OF THE INVENTION

Low birth weight (less than 2500 grams) accounts for seven percent of all births in the United States and is the most important factor associated with infant mortality (National Center for Health Statistics, Healthy People 2000: Maternal and Infant Heath Progress Review, 1999).

Chronic lung disease (CLD), also known as bronchopulmonary dysplasia is a frequent and increasing complication in premature infants, usually presenting within the first 4 weeks after birth. The incidence and severity of CLD is inversely proportional to gestational age. Along with respiratory distress syndrome (RDS; also called hyaline membrane disease), it is one of the leading causes of infant mortality in developed countries (National Heart Lung and Blood Institute, NIH Publication No. 98-4081, 1998). CLD is a common complication in premature infants having RDS, although any newborn with severe respiratory problems is at risk for CLD. RDS occurs during the first several hours after birth and is caused by surfactant deficiency. Lack of surfactant leads to alveoli collapse, decreased lung capacity and edema. Premature infants with RDS have difficulty breathing and have an increased oxygen demand, requiring treatment by supplemental oxygen and mechanical ventilation. Lack of surfactant leads to pulmonary inflammation, which is further exacerbated by oxygen toxicity, barotrauma from mechanical ventilation, and infection (Cole, Exp. Opin. Invest. Drugs 9:53, 2000). Though the pathogenesis of CLD is not fully understood, pulmonary inflammation is a common feature in all infants with the disease. The inflammation and injury leads to delayed pulmonary growth and development.

Postnatal treatment with glucocorticoids reduces the inflammation and swelling of airways in ventilator-dependent low birth weight preterm infants, and results in observable clinical changes including increased pulmonary compliance, decreased airway resistance, and accelerated weaning from mechanical ventilation and supplemental oxygen (Cole, supra). Recent reports show that approximately 40% of extremely low birth weight infants receive such treatment (Barrington, BMC Pediatrics 1:1, 2001). This is significant because extremely low birth weight infants account for approximately 1.4% of the 3.5 million babies born in the United States each year (see, e.g., Barrington, supra).

In most species, including man, the physiological glucocorticoid is cortisol (hydrocortisone). Glucocorticoids are secreted in response to ACTH (adrenocorticotropin), and are responsive within minutes to many physical and psychological stresses, including trauma, surgery, exercise, anxiety and depression. Cortisol acts by binding to an intracellular, glucocorticoid receptor (GR).

It has been postulated that high levels of cortisol are neurotoxic, particularly in the hippocampus, (see, e.g., Sapolsky et al., Ann. NY Acad Sci. 746:294, 1994; Silva, Annu. Rev. Genet. 31:527, 1997; de Leon et al., J. Clin. Endocrinol & Metab. 82:3251, 1997). Studies of human subjects who have received treatment with exogenous glucocorticoids at therapeutic levels have suggested that glucocorticoids may play a role in short-term, reversible memory impairment. (see, e.g., Wolkowitz et al., Am J. Psychiatry 147:1297, 1990; Keenan et al., Neurology 47:1396, 1996; Newcomer et al., Arch Gen. Psychiatry 56:527-533, 1999).

Thus, despite the success of glucocorticoid therapy for treating pulmonary inflammation in ventilator-dependent low birth weight preterm infants, there are growing concerns regarding the short and long term adverse effects experienced by glucocorticoid treated premature infants. Short term adverse effects may include hyperglycemia, hypertension, hypertrophic obstructive cardiomyopathy, gastrointestinal hemorrhage and perforations, growth failure and hypothalamic-pituitary-adrenal axis suppression (see Shah, et al., Cochrane Database Syst. Rev. 1:CD002058, 2003). The long term neurological disorders are however, the most disconcerting adverse effects. Studies of preterm infants demonstrate that in the long term, there are increased rates of cerebral palsy in those receiving treatment versus those not receiving treatment, and probable increases in rates of total neurodevelopmental disability (Barrington, supra). In rats, glucocorticoid administration in the last days of gestation or first two weeks of postnatal life at doses mimicking pulmonary therapy doses, leads to neurological impairment, including acceleration of differentiation of specific target cells in the central nervous system (see, e.g., Carlos, et al., Teratology 46:45, 1992).

Because of the increasing evidence that glucocorticoid treatment affects neurological development, several experts in the field have urged abandoning glucocorticoid treatment altogether, despite its success in reducing inflammation and accelerating the process of weaning infants off of ventilators (See, e.g., Barrington, supra; Shah, supra; Committee on Fetus and Newborn, Pediatrics 109:330, 2002). Thus, while glucocorticoid therapy is a rapid and effective treatment for inflammation, the potential risk for permanent neurological damage threatens to eliminate this promising treatment.

Fortunately, it has now been discovered that inhibition of glucocorticoid receptor activity in the central nervous system of in ventilator-dependent low birth weight preterm infants by concomitant intrathecal administration of antiglucocorticoids during postnatal glucocorticoid therapy can prevent or reverse neurological damage caused by the postnatal glucocorticoid therapy. Thus, the invention fulfills a need for effective methods to prevent damaging neurological side effects of postnatal glucocorticoid therapy while allowing for the maximum benefit of the postnatal glucocorticoid therapy to be realized.

SUMMARY OF THE INVENTION

Accordingly, the present invention provides a method for preventing neurological damage in ventilator-dependent low birth weight preterm infants receiving postnatal glucocorticoid therapy. The method comprises concomitant administration of glucocorticoid receptor antagonists with postnatal glucocorticoids.

In one embodiment, the postnatal glucocorticoid is selected from the group consisting of dexamethasone and betamethasone. In one embodiment initiation of postnatal glucocorticoid therapy occurs within 96 hours after birth. In another embodiment initiation of postnatal glucocorticoid therapy occurs within 3 to 14 days after birth.

In one embodiment, the glucocorticoid receptor antagonist is administered intrathecally. In another embodiment administration of the glucocorticoid receptor antagonist is initiated at the same time as the postnatal glucocorticoid therapy.

In one embodiment, the low birth weight preterm infant weighs 2500 grams or less. In another embodiment, the low birth weight preterm infant weighs 1500 grams or less. In another embodiment the low birth weight preterm infant weighs 1000 grams or less.

In one embodiment, the glucocorticoid receptor antagonist comprises a steroidal skeleton with at least one phenyl-containing moiety in the 11-beta position of the steroidal skeleton. In another embodiment, the phenyl-containing moiety in the 11-beta position of the steroidal skeleton is a dimethylaminophenyl moiety. In a preferred embodiment, the glucocorticoid receptor antagonist comprises mifepristone. In another embodiment, the glucocorticoid receptor antagonist is selected from the group consisting of 11-β-(4-dimethyl-aminoethoxyphenyl)-17α-propynyl-17β-hydroxy-4,9-estra-dien-3-one, and 17β-hydrox-17α-19-(4-methyl-phenyl)androsta-4,9 (11)-dien-3-one.

In one embodiment, the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3, 4,4α,9,10,10α(R)-octahydro-phenanthrene-2,7-diol. In an alternative embodiment, the glucocorticoid receptor antagonist is (11β,17β)-11-(1,3-benzodioxol-5-yl)-17-hydroxy-17-(1-propynyl)estra-4,9-dien-3-one.

The invention also provides a kit for preventing neurological damage in a ventilator dependent low birth weight preterm infant receiving postnatal glucocorticoid therapy, wherein the kit comprises a specific glucocorticoid receptor antagonist, and an instructional material teaching the indications, dosage and schedule of administration for the glucocorticoid receptor antagonist concomitantly with a postnatal glucocorticoid, in a dose effective for preventing neurological damage to the infant from the postnatal glucocorticoid. In one embodiment the glucocorticoid receptor antagonist included in the kit is mifepristone.

Thus, the invention provides a new, effective treatment for the prevention of neurological damage in ventilator-dependent low birth weight preterm infants receiving postnatal glucocorticoid therapy.

DETAILED DESCRIPTION OF THE INVENTION

Definitions

The term "cortisol" refers to a family of compositions also referred to as hydrocortisone, and any synthetic or natural analogues thereof. This includes glucocorticoids (also known as glucocorticosteriods or corticoids).

The term "glucocorticoid receptor" as used herein refers to a family of intracellular receptors also referred to as the cortisol receptor, which specifically bind to cortisol and/or cortisol analogs. The term includes isoforms of glucocorticoid receptors, recombinant glucocorticoid receptors and mutated glucocorticoid receptors.

The terms "glucocorticoid receptor antagonist", "GR antagonist", "antiglucocorticoid", "glucocorticoid blocker" refer to any composition or compound which at least partially inhibits (antagonizes) the biological response that results from the binding of a glucocorticoid receptor agonist, such as cortisol, or cortisol analogs, synthetic or natural, to a glucocorticoid receptor. A "glucocorticoid receptor antagonist" may itself bind a glucocorticoid receptor, or it may inhibit the binding of an agonist to a glucocorticoid receptor, or it may block the downstream biological activities that result from the binding of a glucocorticoid receptor agonist to a glucocorticoid receptor. Thus, a "glucocorticoid receptor antagonist" or "antiglucocorticoid" refers to any composition or compound which inhibits any biological response associated with the binding of a glucocorticoid receptor to an agonist.

The term "mifepristone" refers to a family of compositions also referred to as RU486, or RU38.486, or 17-β-hydroxy-11-β-(4-dimethyl-aminophenyl)-17-α-(1-propynyl)-estra-4, 9-dien-3-one), or 11-β-(4dimethylaminophenyl)-17-β-hydroxy-17-α-(1-propynyl)-estra-4,9-dien-3-one), or analogs thereof, which bind to the glucocorticoid receptor, typically with high affinity, and inhibit the biological effects initiated/mediated by the binding of any cortisol or cortisol analogue to a GR receptor. Chemical names for RU-486 vary; for example, RU486 has also been termed: 11β-[p-(Dimethylamino)phenyl]-17β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one; 17β-hydroxy-11β-(4-dimethylaminophenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-17-hydroxy-17-(1-propynyl)estra-4,9-dien-3-one; and 11β-[4-(N,N-dimethylamino)phenyl]-17α-(prop-1-ynyl)-D-4,9-estradiene-17β-ol-3-one.

The term "neurological damage" as used herein refers to damage to the nervous system, resulting in structural or functional abnormalities. By way of example, but not of limitation, neurological damage may include decreased brain growth, decreased cell numbers in the cerebrum and cerebellum, decreased cerebellar DNA, decreased glucocorticoid receptor activity in the hippocampus, and decreased myelination. Neurological damage may also manifest itself as reduced premature brain size, cerebral palsy, abnormal motor activity, retinopathies, or cognitive deficits. Methods for measuring neurological damage are known in the art.

The term "cerebral palsy" refers to a group of chronic disorders impairing control of movement that generally do not worsen, but may change over time. Symptoms include difficulty with fine motor tasks, difficulty maintaining balance or walking, involuntary movements. The exact symptoms differ from person to person.

The term "prevention" refers to any indicia of success in prevention, treatment or amelioration of neurological damage, injury, pathology or condition, including any objective or subjective parameter such as abatement; remission; diminishing of symptoms, prevention or lessening of neurological damage or injury, making the condition more tolerable to the infant; making the final point of degeneration less debilitating; improving a patient's physical or mental well-being. For example, success of treatment by methods of the invention could be measured by comparison to ventilator-dependent low birth weight preterm infants who did not receive concomitant administration of antiglucocorticoids with postnatal glucocorticoid therapy. The prevention, treatment or amelioration of symptoms can be based on objective or subjective parameters; including the results of a physical examination, biopsy or microscopic examination of a tissue sample, or any other appropriate means known in the art.

The term "preterm infant" refers to an infant born before 37 weeks of gestation. This includes terms such as premature infant or preemie. The term "low birth weight preterm infant" refers to a preterm infant weighing less than 2,500 grams at birth. This term includes preterm infants described as low birth weight (less than 2,500 grams), very low birth weight (less than 1,500 grams) and extremely low birth weight (less than 1,000 grams).

The term "ventilator" refers a device for maintaining artificial respiration such as a mechanical ventilator, also called a respirator. The term "ventilator-dependent" refers to the requirement for a mechanical means of ventilation to maintain respiration.

The term "postnatal glucocorticoid therapy" refers to the administration of glucocorticoids after birth. The postnatal glucocorticoid therapy may be administered for the purpose of preventing chronic lung disease in a preterm infant, or may be given for any other purpose known in the art. Postnatal glucocorticoid therapy comprises both inhaled and systemic treatment, and may be initiated any time between birth and 14 days after birth. The term "postnatal glucocorticoid therapy" includes, but is not limited to therapy delivered within 96 hours of birth as well as that which is initiated 3-14 days after birth. Postnatal glucocorticoid therapy can be administered prophylactically or therapeutically. Typically prophylactic therapy is initiated within 3 days or less after birth, before the infant shows any signs of chronic lung disease or other symptoms that may indicate the need for postnatal treatment with glucocorticoids. Postnatal glucocorticoid therapy may also be initiated therapeutically in response to symptoms. The term "postnatal glucocorticoid" refers to any glucocorticoid delivered at any time between birth and 14 days.

The term "concomitant administration" of glucocorticoid receptor antagonist with a postnatal glucocorticoid refers to administration of the glucocorticoid receptor antagonist and the postnatal glucocorticoid at such times that both the postnatal glucocorticoid and glucocorticoid receptor antagonist can reach a therapeutically effective amount at an appropriate time relative to one another. Although concomitant administration typically involves concurrent (i.e. at the same time), administration of the antiglucocorticoid with respect to the administration of the postnatal glucocorticoid, antiglucocorticoid may also be concomitantly administered prior to or subsequent to the initiation of glucocorticoid therapy if such timing is required for the postnatal glucocorticoid and glucocorticoid receptor antagonist to reach a therapeutically effective amount at an appropriate time relative to one another. A person of ordinary skill in the art, based on the information provided herein and having knowledge of the postnatal glucocorticoid and of central nervous system administration of glucocorticoid receptor antagonists, will have no difficulty determining the appropriate timing, sequence, and dosages for administration of the glucocorticoid receptor antagonist with respect to the dosage of the postnatal glucocorticoid.

The term "intrathecally" refers to introduction into or occurrence in the space under the arachnoid membrane of the brain or spinal cord. The term "intrathecal administration" is intended to include delivering a formulation directly into the cerebrospinal fluid of a subject, by techniques that include what is understood in the art to comprise intrathecal injection, as well as lateral cerebroventricular injection (described in Lazorthes et al. Advances in Drug Delivery Systems and Applications in Neurosurgery, 143-192 and Omaya et al., Cancer Drug Delivery, 1: 169-179). Administration can be achieved by direct injection of the formulation or by the use of infusion pumps. The injection can be, for example, in the form of a bolus injection or continuous infusion (e.g., using infusion pumps).

Introduction

The invention provides a method for preventing neurological damage in a ventilator dependent low birth weight preterm infant receiving postnatal glucocorticoid therapy. The method comprises administering a glucocorticoid receptor antagonist concomitant with a postnatal glucocorticoid in a dose effective for preventing neurological damage to the infant from the postnatal glucocorticoid.

Glucocorticoids are used in the neonatal period to treat or prevent chronic lung disease (CLD) in preterm babies. As noted earlier, glucocorticoid therapy may prevent or treat chronic lung disease in the preterm infant, but glucocorticoid use may be associated with certain adverse effects such as neurological damage and developmental delays.

It has now been discovered that the neurological damage that may occur as a result of glucocorticoid administration to preterm infants can be prevented by administration of an antiglucocorticoid concomitant with the glucocorticoid therapy. In a preferred embodiment, the antiglucocorticoid is administered by direct injection into the cerebrospinal fluid of the infant.

In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways. Glucocorticoids bind the receptors thereby acting as agonists to activate a biological response.

The biologic effects of glucocorticoids such as dexamethasone and betamethasone, including pathologies or dysfunctions that may develop in a preterm infant receiving glucocorticoid therapy, can be modulated and controlled at the glucocorticoid receptor level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation <$10^{-9}$ M (Cadepond, *Annu. Rev. Med* 48:129, 1997). Thus, in one embodiment of the invention, mifepristone and related compounds are administered to low birth weight preterm infants who are receiving postnatal glucocorticoid therapy, to prevent neurological damage in the infant.

As the methods of the invention include use of any means to inhibit the biological effects of an agonist-bound GR, illustrative compounds and compositions which can be used to treat and thereby prevent neurological damage in low birth weight preterm infants receiving postnatal glucocorticoid therapy are set forth, but these illustrations are not meant to be limiting. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are also set forth below.

Diagnosing Ventilator-Dependant Low Birth Weight Preterm Infants in Need of Antiglucocorticoid Treatment to Prevent Neurological Damage A. Assessing and Diagnosing Preterm Infants in Need of Anti-Glucocorticoid Treatment Any infant receiving glucocorticoid therapy would benefit from antiglucocorticoid treatment according to the methods of the invention. However, ventilator-dependent low birth weight preterm infants receiving postnatal glucocorticoid therapy to treat or prevent chronic lung disease are preferred candidates.

The infant may be receiving postnatal glucocorticoid treatment as prophylactic therapy, wherein the glucocorticoid therapy was initiated before the infant showed any signs of respiratory distress syndrome or chronic lung disease, or the infant may be in early therapy for the treatment of disease symptoms. In cases where the infant is in early therapy the infant is typically 3-14 days old. The infant may be receiving postnatal glucocorticoid therapy by any means known in the art. For example, the glucocorticoid treatment can be administered systemically in pulses or by tapering over time or it can be administered by aerosol inhalation. In some cases the postnatal glucocorticoid therapy comprises the administration of dexamethasone or betamethasone.

Treatment of Ventilator-Dependant Low Birth Weight Preterm Infants Receiving Postnatal Glucocorticoid Therapy with Glucocorticoid Receptor Antagonists I. Glucocorticoid Receptor Antagonists to Reduce Neurological Damage The invention provides a method of preventing neurological damage in ventilator-dependant low birth weight preterm infants who are receiving postnatal glucocorticoid therapy. The method provides utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

A. Steroidal Antiglucocorticoids as GR Antagonists.

Steroidal glucocorticoid antagonists are administered to prevent neurological damage in low birth weight preterm infants in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

Examples of steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127 and U.S. Pat. No. 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl)androsta-4,9 (11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., *Int'l J. of Neuro-psychopharmacology*, 5:Supp. 1, S148 (2002); disclose the compound (11β,17β)-11-(1,3-benzodioxol-5-yl)-17-hydroxy-17-(1-propynyl)estra-4,9-dien-3-one (ORG 34517) which in a preferred embodiment, is administered in an amount effective to prevent neurological damage in a preterm infant receiving postnatal glucocorticoid therapy.

1. Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, FEBS 217:221-226, 1987). Another preferred embodiment comprises an 11-beta phenyl-aminodimethyl steroid backbone derivative, i.e., mifepristone, which is both an effective antiglucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, J. Steroid Biochem. Molec. Biol. 45:205-215, 1993). Another GR antagonist related to RU486 is RU044 (RU43.044) 17-beta-hydrox-17-alpha-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible antiglucocorticoids. Such compounds include alpha-keto-methanesulfonate derivatives of cortisol, including cortisol-21-mesylate (4-pregnene-11-beta,17-alpha,21-triol-3,20-dione-21-methane-sulfonate and dexamethasone-21-mesylate (16-methyl-9 alpha-fluoro-1,4-pregnadiene-11 beta, 17-alpha, 21-triol-3,20-dione-21-methane-sulfonate). See Simons, *J. Steroid Biochem.* 24:25-32, 1986; Mercier, *J. Steroid Biochem.* 25:11-20, 1986; U.S. Pat. No. 4,296,206.

2. Modification of the 17-Beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17,21-acetonide derivatives and 17-beta-carboxamide derivatives of dexamethasone (Lefebvre, 1989, supra; Rousseau, *Nature* 279:158-160, 1979).

3. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, J Steroid Biochem Mol Biol 42(7):695-704, 1992), RU43044, RU40555 (see Kim, J Steroid Biochem Mol Biol. 67(3):213-22, 1998), RU28362, and ZK98299.

B. Non-Steroidal Antiglucocorticoids as Antagonists.

Non-steroidal glucocorticoid antagonists are also used in the methods of the invention to prevent neurological damage in low birth weight preterm infants. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, Int. J. Pept. Protein Res. 43:297-304, 1994; de Bont, Bioorganic & Medicinal Chem. 4:667-672, 1996). The creation and simultaneous screening of large libraries of synthetic molecules can be carried out using well-known techniques in combinatorial chemistry, for example, see van Breemen, Anal Chem 69:2159-2164, 1997; and Lam, Anticancer Drug Des 12:145-167, 1997. Design of peptidomimetics specific for GR can be designed using computer programs in conjunction with combinatorial chemistry (combinatorial library) screening approaches (Murray, of Computer-Aided Molec. Design 9:381-395, 1995; Bohm, J. of Computer-Aided Molec. Design 10:265-272, 1996). Such "rational drug design" can help develop peptide isomerics and conformers including cycloisomers, retro-inverso isomers, retro isomers and the like (as discussed in Chorev, TibTech 13:438-445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl]diphenyl)methyl)imidazole; N-(2[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4¦]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl)methylimidazole (see U.S. Pat. No. 6,051,573); the GR antagonist compounds disclosed in U.S. Pat. Nos. 5,696,127 and 6,570,020; the GR antagonist compounds disclosed in US Patent Application 20020077356, the glucocorticoid receptor antagonists disclosed in Bradley et al., J. Med Chem. 45, 2417-2424 (2002), e.g., 4α(S)-Benzyl-2(R)-chloroethynyl-1,2,3,4,4α,9,10,10α(R)-octahydro-phenanthrene-2,7-diol ("CP 394531") and 4α(S)-Benzyl-2(R)-prop-1-ynyl-1,2,3,4,4α,9,10,10α(R)-octahydro-phenanthrene-2,7-diol ("CP 409069"); the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., Endocrin., 141:2294-2300 (2000).

Glucocorticoid Receptor Antagonists as Pharmaceutical Compositions

Glucocorticoid receptor antagonists can be prepared as pharmaceutical formulations according to any method known to the art for the manufacture of pharmaceuticals. Such drugs can contain coloring agents and preserving agents. Any glucocorticoid receptor antagonist formulation can be admixtured with nontoxic pharmaceutically acceptable excipients which are suitable for manufacture.

Compositions comprise at least one compound of this invention in combination with at least one pharmaceutically acceptable excipient. Suitable excipients are well known to persons of ordinary skill in the art, and they, and the methods of formulating the compositions, may be found in such standard references as Remington's, supra. Suitable liquid carriers, especially for injectable solutions, include water, aqueous saline solution, aqueous dextrose solution, and glycols.

Aqueous suspensions of the invention contain a glucocorticoid receptor antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate or one or more coloring agents. Formulations can be adjusted for osmolarity.

Oil suspensions can be formulated by suspending a glucocorticoid receptor antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. These formulations can be preserved by the addition of an antioxidant such as ascorbic acid. As an example of an injectable oil vehicle, see, e.g., Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. Such formulations can also contain a demulcent, a preservative, or a coloring agent.

In another embodiment, the GR antagonist formulations of the invention are useful for administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs.

After a pharmaceutical comprising a glucocorticoid receptor antagonist of the invention has been formulated in a acceptable carrier, it can be placed in an appropriate container and labeled for treatment of an indicated condition. For administration of glucocorticoid receptor antagonists, such labeling would include, e.g., instructions concerning the amount, frequency and method of administration. In one embodiment, the invention provides for a kit for preventing neurological damage in a low birth weight preterm infant receiving glucocorticoid therapy which includes a glucocorticoid receptor antagonist and instructional material teaching the indications, dosage and schedule of administration of the glucocorticoid receptor antagonist.

Determining Dosing Regimens for Glucocorticoid Receptor Antagonists

The methods of the invention prevent neurological damage in a low birth weight preterm infant receiving postnatal glucocorticoid therapy. The amount of glucocorticoid receptor antagonist adequate to accomplish this is defined as a "therapeutically effective dose", or an "effective dose". The dosage schedule and amounts effective for this use, i.e., the "dosing regimen," will depend upon a variety of factors, including the mode of administration of the antiglucocorticoid, the existence or severity chronic lung disease, the dose of glucocorticoids, the birth weight of the infant, as well as the infant's physical status, age and the like.

The state of the art allows the clinician to determine the dosage regimen for each individual infant, taking into consideration the particular glucocorticoid receptor antagonist to be used for the prevention of neurological damage, as well as the particular glucocorticoid being administered as postnatal glucocorticoid therapy. Indeed, the therapeutically effective dosage of antiglucocorticoid will take into consideration the nature, identity and dosage of the postnatal glucocorticoid. Typically, postnatal glucocorticoid is administered to a preterm infant in amounts ranging from about 0.5 µg to about 1 mg/kg of body weight per infant per day, sometimes between about 15 µg to about 750 µg/kg of body weight per infant per day, or perhaps about 20 µg to about 500 µg/kg of body weight per infant per day. The glucocorticoid may be administered in a range of concentrations over a period of time, and may remain constant over a period of time or could taper.

Effective intrathecal doses of antiglucocorticoid are significantly lower than effective systemic doses (see e.g., De Kloet E R, et al. (1988) Neuroendocrinology 47:2 109-15; Ratka A, et al. (1989) Neuroendocrinology 50:2 117-23 and Aernout, D. et al. (1996) Endocrinology 137(11):4935-4943). Therefore, the precise dosage for an antiglucocorticoid will typically be lower than the dosages recited above for postnatal glucocorticoids. Other factors to be considered in calculating the dose of antiglucocorticoid include the relative affinities of the glucocorticoid and the antiglucocorticoid for the glucocorticoid receptor (as reflected in the relative dissociation constants), the half lives of the glucocorticoid and the antiglucocorticoid, and the ease with which the glucocorticoid crosses the blood brain barrier. By evaluating an infant using the methods described herein, a skilled practitioner will be able to determine whether a patient is responding to treatment and will know how to adjust the dosage levels accordingly.

The following provides an example of how one of skill can determine the initial amount of antiglucocorticoid to be intrathecally administered to the ventilator-dependent preterm infant. A dose of glucocorticoid for a preterm infant might be 500 µg/kg/day, administered such that the plasma concentration reaches a peak of 250 ng/ml within 30 minutes of intravenous systemic dosing. If the glucorticoid traverses the blood brain barrier readily, but not 100% efficiently, this may correspond to a peak concentration in the cerebrospinal fluid of 50 ng/ml. However, the actual concentration can be measured by methods known in the art. If the rate of dosing is such that the plasma and cerebrospinal fluid concentrations of the glucocorticoid are maintained at their peak levels once achieved, and the $K_d$ for glucocorticoid-glucocorticoid receptor interaction is $10^{-8}$, then the concentration and dosing rate of the therapeutically effective dose antiglucocorticoid can readily be calculated.

To ensure that the antiglucocorticoid is present in the cerebrospinal fluid at the time the glucocorticoid starts to become available to the glucocorticoid receptors of the central nervous system, administration of the antiglucocorticoid should begin concomitant with glucocorticoid administration. If the antiglucocorticoid is chosen such that the $K_d$ for dissociation of the antiglucocorticoid-glucocorticoid receptor complex is at least 10-fold lower than the $K_d$ for dissociation of the glucocorticoid-glucocorticoid receptor complex (i.e. the complex is stronger), then when both the glucocorticoid and the glucocorticoid receptor antagonist are present at similar concentrations at equilibrium, at least 90% of the glucocorticoid receptor binding sites will be occupied by antiglucocorticoid molecules, thus effectively blocking the action of glucocorticoids in the central nervous system. In this example, the intrathecal dosage of the antiglucocorticoid would be adjusted, based on the estimated volume of the infant's cerebrospinal fluid, to achieve a concentration of 50 ng/ml.

The antiglucocorticoid may be administered in a range of concentrations that parallel the dosage of postnatal glucocorticoid, albeit at a lower level, over a period of time. For example, an infant could receive an initial concomitant intrathecal dose ranging from 150 ng/kg/day up to 600 ng/kg/day, over a period of days, to parallel a dosing schedule of postnatal glucocorticoid consisting of 45 µg/kg/day to 180 µg/kg/day. The dosage may remain constant over a period of time or could taper. Other dosages possible, and can be determined by a skilled practitioner according to the disclosure provided herein and the needs of a particular infant.

In summary, the effective intrathecal dose of antiglucocorticoid will be small relative to the dosage of postnatal glucocorticoid. Therefore, systemic plasma glucocorticoid concentrations will be significantly greater than plasma antiglucocorticoid concentrations that might arise from leakage of antiglucocorticoid out of the cerebrospinal fluid. Thus, regardless of whether or not the antiglucocorticoid readily crosses the blood brain barrier, intrathecal administration provides an effective route for administration of the antiglucocorticoid that permits dosing effective to prevent neurological damage associated with postnatal glucocorticoids and at the same time allows the maximum systemic benefit of the postnatal glucocorticoid to be realized.

Methods of Administration

In general, antiglucocorticoid compounds may be administered as pharmaceutical compositions by any method known in the art for administering therapeutic drugs. However, the glucocorticoid receptor antagonists used in the methods of the invention are preferably administered directly into the cerebrospinal fluid by intrathecal injection.

Single or multiple administrations of glucocorticoid receptor antagonist formulations can be administered depending on the frequency, amount of dosage, and half life of the postnatal glucocorticoid. Typically the dosage of the glucocorticoid receptor antagonist formulation will be at a similar frequency, but in a significantly lower amount than the postnatal glucocorticoid (De Kloet E R, et al. (1988) Neuroendocrinology 47:2 109-15; Ratka A, et at. (1989) Neuroendocrinology 50:2 117-23 and Aernout, D. et al. (1996) Endocrinology 137(11):4935-4943). In general, the amount of antiglucocorticoid to be administered to the infant will be at least a 5-fold lower than the amount of postnatal glucocorticoid, but may be in an amount that is 25-fold, 250-fold, 1000-fold, 100,000-fold or even more fold lower than the postnatal glucocorticoid. Most importantly, the formulations should provide a sufficient quantity of active agent, e.g., mifepristone, to effectively prevent neurological damage caused by postnatal glucocorticoid therapy in ventilator dependent low birth weight preterm infants.

A typical pharmaceutical formulation for intrathecal administration of an antiglucocorticoid such as mifepristone or ORG 34517 would comprise about 10 ng-4 µg mifepristone or ORG 34517 per kg of body weight per infant per day, more preferably between about 60 ng to about 3 µg mifepristone or ORG 34517 per kg of body weight per infant per day, most preferably 500 ng mifepristone or ORG 34517 per kg of body weight per infant per day, although dosages of between about 5 ng to about 40 µg mifepristone or ORG 34517 per kg of body weight per infant per day may be used in the practice of the invention. Such a dose is significantly lower than the doses of postnatal glucocorticoid typically provided for postnatal glucocorticoid therapy.

2. General Laboratory Procedures

When practicing the methods of the invention, a number of general laboratory tests can be used to assist in the diagnosis, progress and prognosis of a low birth weight preterm infant at risk for neurological damage, including monitoring of parameters such as blood and plasma glucocorticoids and antiglucocorticoids, drug metabolism, brain structure and function and the like. These procedures can be helpful because all patients metabolize and react to drugs uniquely. In addition, such monitoring may be important because each GR antagonist has different pharmacokinetics. Different patients may require different dosage regimens and formulations. A few illustrative examples are set forth below.

a. Determination of Glucocorticoid or Antiglucocorticoid Levels in Cerebrospinal Fluid It may be necessary to measure levels of glucocorticoid or antiglucocorticoid in cerebrospinal fluid, as well as in the blood and plasma. Means for such monitoring are well described in the scientific and patent literature. An illustrative example of determining levels of glucocorticoid or antiglucocorticoid in cerebrospinal fluid is set forth in Example 2 below.

b. Assessing Reduction in Neurological Damage

Assessing the success of concomitant administration of an antiglucocorticoid in the prevention of neurological damage in ventilator-dependent preterm infants receiving postnatal glucocorticoid therapy may be determined by comparing those infants with those receiving only glucocorticoid therapy. Methods for evaluating neurological damage are readily determined by those skilled in the art. By way of example but not of limitation, the types of damage that may be expected include decreased premature brain size, increased rates of cerebral palsy, cognitive deficits or retinopathies. Methods for evaluating neurological damage could include, but are not limited to, 3d magnetic resonance imaging to quantify cerebral tissue, determination of Bayley II Mental Developmental Index, determination of Psychomotor Developmental Index, tests for vision or hearing impairment.

d. Other Laboratory Procedures

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

EXAMPLES

Example 1

Preventing Neurological Damage in a Subject Using Mifepristone

The following example demonstrates how to practice the methods of the invention.

Patient Selection:

Ventilator-dependent low birth weight preterm infants 0-14 days old in need of glucocorticoid therapy using the methods described herein.

Dosage Regimen and Intrathecal Administration of Mifepristone Concomitantly with Glucocorticoid Therapy:

The glucocorticoid receptor (GR) antagonist, mifepristone, is used concomitantly with the glucocorticoid dexamethasone in this study. Glucocorticoid therapy is initiated at 0-14 days of age; with dexamethasone being administered intravenously at a dose of about 500 µg/kg/day for approximately 5 days.

Mifepristone administration is initiated intrathecally within approximately 15 minutes of the start of glucocorticoid therapy, at a dose that is 1000-fold lower than the dosage of the postnatal dexamethasone. At this dosage, mifepristone will block postnatal glucocorticoid action in the central nervous system, while remaining at very low systemic concentrations (Aernout, D. et al. (1996) Endocrinology 137(11): 4935-4943, and De Kloet E R, et al. (1988) Neuroendocrinology 47:2 109-15). Dosages will be adjusted if necessary and further evaluations will be performed periodically throughout treatment. Infants will receive concomitant administration of mifepristone for the duration of the postnatal glucocorticoid therapy, and will be evaluated as described below.

Assessing Prevention of Neurological Damage:

To delineate and assess the effectiveness of mifepristone in preventing neurological damage, the neurological damage is determined by objective and subjective criteria as described herein Tests for neurological damage may include tests for cerebral palsy, cognitive deficits or retinopathies. In addition, neurological damage could be detected by 3d magnetic resonance imaging to quantify cerebral tissue, determination of Bayley II Mental Developmental Index, determination of Psychomotor Developmental Index, tests for vision or hearing impairment. Tests for neurological damage will be measured at baseline, 2 weeks, 1 month, 2 months, 3 months, and 6 months.

Example 2

Measuring Levels of Glucocorticoid or Antiglucocorticoid in Cerebrospinal Fluid

The concentration of glucocorticoids or antiglucocorticoids in the cerebrospinal fluid of the infants of Example 1 will be tested before initiation of postnatal glucocorticoid therapy, immediately after initiation of postnatal glucocorticoid therapy, and as necessary during the course of postnatal glucocorticoid therapy and administration of antiglucocorticoid. A lumbar reservoir is surgically implanted into the lower back to sample cerebrospinal fluid and to administer the antiglucocorticoid into the cerebrospinal fluid.

Samples of cerebrospinal fluid will be tested for the absence or presence of and of glucocorticoids and antiglucocorticoids in the cerebrospinal fluid and to measure the concentration of glucocorticoids and antiglucocorticoids when present. Methods for measuring the presence and concentration of glucocorticoids and antiglucocorticoids in samples are well known in the art. For example, the concentration of glucocorticoids and antiglucocorticoids can be measured using HPLC, TLC and/or UV spectroscopy, although and method known in the art for detecting the presence of glucocorticoids and antiglucocorticoids may be used.

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method for inhibiting glucocorticoid induced neurological damage in a ventilator dependent low birth weight preterm infant receiving postnatal glucocorticoid therapy, comprising: administering by intrathecal injection a glucocorticoid receptor antagonist concommitantly with a postnatal glucocorticoid in a dose effective for inhibiting neurological damage to the infant from the postnatal glucocorticoid wherein the glucocorticoid receptor antagonist is administered at a dose at least 5 fold lower than the dose of postnatal glucocorticoid.

2. The method of claim 1, wherein the postnatal glucocorticoid therapy comprises administration of a glucocorticoid selected from the group consisting of dexamethasone and betamethasone.

3. The method of claim 1, wherein the postnatal glucocorticoid therapy is initiated within 96 hours of birth.

4. The method of claim 1, wherein the postnatal glucocorticoid therapy is initiated 3-14 days after birth.

5. The method of claim 1, wherein concomitant administration of the glucocorticoid receptor antagonist is initiated at the same time as the postnatal glucocorticoid therapy.

6. The method of claim 1, wherein the low birthweight infant weighs 2500 grams or less at birth.

7. The method of claim 1, wherein the low birthweight infant weighs 1500 grams or less at birth.

8. The method of claim 1, wherein the low birthweight infant weighs 1000 grams or less at birth.

9. The method of claim 1, wherein the glucocorticoid receptor antagonist comprises a steroidal skeleton with at least one phenyl-containing moiety in the 11-beta position of the steroidal skeleton.

10. The method of claim 1, wherein the phenyl-containing moiety in the 11-beta position of the steroidal skeleton is a dimethylaminophenyl moiety.

11. The method of claim 10, wherein the glucocorticoid receptor antagonist comprises mifepristone.

12. The method of claim 10, wherein the glucocorticoid receptor antagonist is selected from the group consisting of 11β-(4-dimethylaminoethoxyphenyl)-17α-propynyl-17β-hydroxy-4,9 estradien-3-one and 17β-hydroxy-17α-19-(4-methylphenyl)androsta-4,9(11)-dien-3-one.

13. The method of claim 1 wherein the glucocorticoid receptor antagonist is selected from the group consisting 4α(S)-Benzyl-2(R)-prop-1-ynyl-1,2,3,4,4α,9,10,10a(R)-octahydro-phenanthrene-2,7-diol and 4α(S)-Benzyl-2(R)-chloroethynyl-1,2,3,4,4α,9,10,10a(R)-octahydro-phenanthrene-2,7-diol.

14. The method of claim 1, wherein the glucocorticoid receptor antagonist is (11β,17β)-11-(1,3-benzodioxol-5-yl)-17-hydroxy-17-(1-propynyl)estra-4,9-dien-3-one.

15. The method of claim 1 wherein the glucocorticoid receptor antagonist is administered at a dose at least 250 fold lower than the amount of postnatal glucocorticoid.

* * * * *